United States Patent
Glasgow et al.

(10) Patent No.: US 9,613,516 B2
(45) Date of Patent: Apr. 4, 2017

(54) SYSTEM AND METHODS FOR SOILED GARMENT DETECTION AND NOTIFICATION

(71) Applicant: eBay Inc., San Jose, CA (US)

(72) Inventors: Dane Glasgow, Los Altos, CA (US); Corinne Elizabeth Sherman, San Jose, CA (US); David Ramadge, San Jose, CA (US); Timothy Carlson, Menlo Park, CA (US); Sergio Pinzon Gonzales, Jr., San Jose, CA (US)

(73) Assignee: eBay Inc., San Jose, CA (US)

(*) Notice: Subject to any disclaimer, the term of this patent is extended or adjusted under 35 U.S.C. 154(b) by 76 days.

(21) Appl. No.: 14/663,204

(22) Filed: Mar. 19, 2015

(65) Prior Publication Data

US 2016/0275775 A1 Sep. 22, 2016

(51) Int. Cl.
| | |
|---|---|
| G08B 23/00 | (2006.01) |
| G08B 21/18 | (2006.01) |
| G01N 33/00 | (2006.01) |
| G08C 19/04 | (2006.01) |
| G08B 21/00 | (2006.01) |
| G08B 1/08 | (2006.01) |

(52) U.S. Cl.
CPC ....... *G08B 21/182* (2013.01); *G01N 33/0001* (2013.01)

(58) Field of Classification Search
CPC .. G08B 21/182; A41D 27/00; A41D 2400/00; G01N 33/001
USPC ...................................................... 340/573.1
See application file for complete search history.

(56) References Cited

U.S. PATENT DOCUMENTS

| | | | |
|---|---|---|---|
| 6,006,583 A | 12/1999 | Hayashi | |
| 8,006,542 B2 | 8/2011 | Jones | |
| 8,273,298 B2 | 9/2012 | Newell | |
| 2002/0069465 A1* | 6/2002 | Chute | D06F 58/203 8/158 |
| 2004/0100376 A1* | 5/2004 | Lye | A61B 5/411 340/539.12 |
| 2006/0169796 A1* | 8/2006 | Timpson | A61L 9/042 239/53 |
| 2008/0058744 A1* | 3/2008 | Tippey | A61F 13/42 604/361 |
| 2009/0152310 A1 | 6/2009 | Schawbel | |
| 2011/0008212 A1 | 1/2011 | Ichimura | |
| 2011/0296703 A1* | 12/2011 | Kim | D06F 73/02 34/89 |
| 2013/0086830 A1* | 4/2013 | Moon | D06F 73/02 38/1 A |

(Continued)

*Primary Examiner* — Jack K Wang
(74) *Attorney, Agent, or Firm* — Schwegman Lundberg & Woessner, P.A.

(57) ABSTRACT

Aspects of the present disclosure involve an apparatus, systems, and methods for soiled garment detection and notification. The method may include receiving a measure of odor being released from a garment from a soiled garment detection apparatus. The method may further include determining that the measure of odor exceeds an acceptable odor threshold. A message may then be sent to a user device associated with the garment (e.g. a device of the owner of the garment) in response to determining that the measure of odor exceeds the threshold. The message may include a notification that the garment is soiled, and a suggested course of action to improve the measure of odor released by the garment.

19 Claims, 8 Drawing Sheets

(56) References Cited

U.S. PATENT DOCUMENTS

| | | | |
|---|---|---|---|
| 2013/0107042 A1* | 5/2013 | Forster | G06K 19/07713 348/143 |
| 2014/0070957 A1* | 3/2014 | Longinotti-Buitoni | A61B 5/6804 340/870.01 |
| 2014/0214697 A1* | 7/2014 | McSweeney | B65F 1/004 705/308 |
| 2014/0318699 A1* | 10/2014 | Longinotti-Buitoni | A61B 5/0002 156/247 |
| 2015/0087935 A1* | 3/2015 | Davis | A61B 5/14532 600/309 |
| 2015/0250420 A1* | 9/2015 | Longinotti-Buitoni | A61B 5/6804 600/301 |
| 2015/0272364 A1* | 10/2015 | Larsen | A47G 25/14 223/96 |
| 2016/0113285 A1* | 4/2016 | Goda | A01N 59/00 424/76.1 |
| 2016/0171486 A1* | 6/2016 | Wagner | G06Q 20/12 705/39 |
| 2016/0191511 A1* | 6/2016 | Tijerina | A61B 5/02055 726/7 |

* cited by examiner

SYSTEM AND METHODS FOR SOILED GARMENT DETECTION AND NOTIFICATION

TECHNICAL FIELD

The present application relates to data processing. In particular, example embodiments relate to systems and methods for soiled garment detection and notification.

BACKGROUND

Clothing manufacturers, such as high-end blue jean manufacturers, recommend avoiding laundering certain types of garments after each wear, and instead recommend that garments be laundered much less frequently (e.g., every six months). Further, seasonal garments and other outerwear, such as heavy jackets, often go through many wear cycles without being laundered, if at all. Moreover, energy coconscious consumers may wear garments many times before laundering in an effort to avoid frequent use of laundering devices (e.g., clothes washers and dryers) that use large amounts of energy. Such laundering strategies may cause infrequently laundered garments to become soiled and malodorous, which would otherwise signal the need to launder the garment. However, the odor of the garment may not be apparent to the garment's wearer as the wearer may have become accustomed to the smell over time.

BRIEF DESCRIPTION OF THE DRAWINGS

Various ones of the appended drawings merely illustrate example embodiments of the present disclosure and cannot be considered as limiting its scope.

DETAILED DESCRIPTION

Reference will now be made in detail to specific example embodiments for carrying out the inventive subject matter. Examples of these specific embodiments are illustrated in the accompanying drawings. It will be understood that these examples are not intended to limit the scope of the claims to the illustrated embodiments. On the contrary, they are intended to cover alternatives, modifications, and equivalents as may be included within the scope of the disclosure. In the following description, specific details are set forth in order to provide a thorough understanding of the subject matter. Embodiments may be practiced without some or all of these specific details.

Aspects of the present disclosure involve an apparatus, systems, and methods for detecting soiled garments and providing alerts relating thereto. For the purpose of the present disclosure, the term "soiled" is used to refer to a garment that is unclean and in need of laundering. For the purpose of the present disclosure, the term "launder" is used in various tenses to refer to a process of making garments (e.g., clothes) or household linens (e.g., sheets and towels) ready for use including the steps of sorting, washing, drying, folding, hanging, ironing and steaming. Further, as used herein, the term "launderer" refers to a person performing or engaged in the process of laundering whether through utilization of one or more laundering devices or by hand. The term "laundering device" refers to any device or piece of equipment used in the process of laundering. Laundering devices may, for example, include washing machines (also referred to as a "laundry machine," a "clothes washer," or simply a "washer"), clothes dryers (also referred to as a "tumble dryer," a "drying machine" or simply a "dryer"), clothes iron (also referred to as a "flatiron" or simply an "iron"), a steamer, or a dry cleaning machine.

Example embodiments involve a controller in communication with one or more soiled garment detection apparatus. The soiled garment detection apparatus may be included as part of or affixed to a clothes hanger or laundering device, and is configured to measure an amount of odor released from a garment. The controller uses odor information received from the soiled garment detection apparatus to determine whether the garment is soiled, and therefore in need of laundering. Upon determining that a garment has been soiled, the controller causes a message (e.g., a push notification) to be provided to a device of the owner to remind the owner to launder the garment. Further, the controller may cause a human perceivable alert (e.g., a flashing light) to be provided by the soiled garment detection apparatus associated with the garment to alert the owner of the garment that the garment is soiled.

Figure 1:
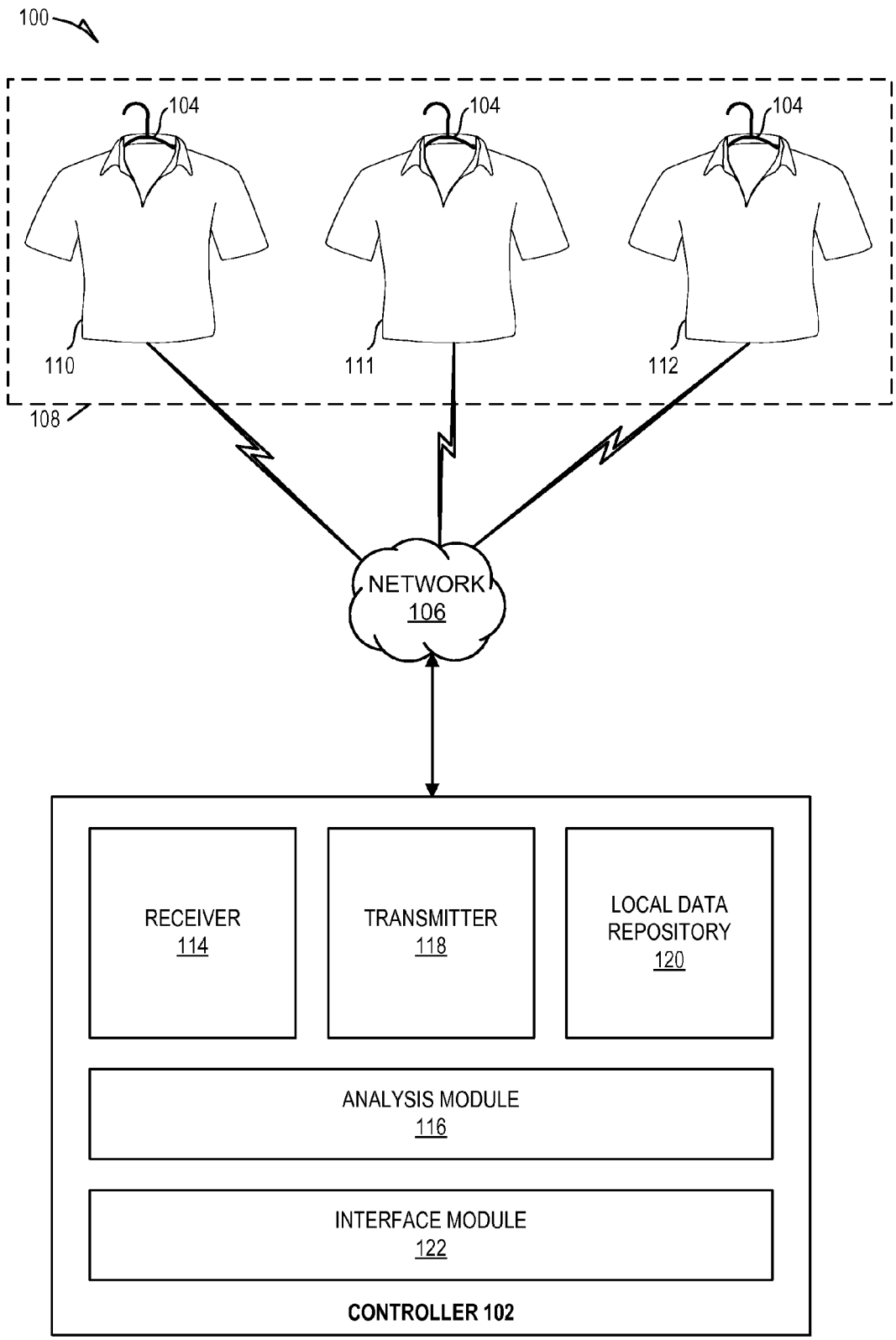
FIG. 1 is a system diagram illustrating a soiled garment detection and notification system, according to an example embodiment.

FIG. 1 is a system diagram illustrating a soiled garment detection and notification system 100, according to an example embodiment. To avoid obscuring the inventive subject matter with unnecessary detail, various functional components (e.g., modules and engines) that are not germane to conveying an understanding of the inventive subject matter have been omitted from FIG. 1. However, a skilled artisan will readily recognize that various additional functional components may be supported by the soiled garment detection and notification system 100 to facilitate additional functionality that is not specifically described herein.

As shown, the soiled garment detection and notification system 100 includes a controller 102 in communication with a plurality of soiled garment detection apparatus 104 over a network 106. The network 106 may be a personal area network implemented, for example, using the ZigBee data transmission protocol. The plurality of soiled garment detection apparatus 104 is associated with a collection of garments 108 comprising garments 110-112. More specifically, an instance of the soiled garment detection apparatus 104 is associated with each of the garments 110-112 by virtue of each of the garments 110-112 being placed within range of the soiled garment detection apparatus 104, which, in the embodiment illustrated in FIG. 1, is in the form of a clothes hanger. Although the soiled garment detection apparatus 104 is illustrated to resemble a clothes hanger suitable for hanging the collection of garments 108 in a closet, for example, the soiled garment detection apparatus 104 is not limited to such a structure, and may, in other embodiments, take another form that is suitable for inclusion in dresser drawers or other storage components used to store garments.

Each instance of the soiled garment detection apparatus 104 is configured to produce a plurality of output signals (e.g., electrical signals) that collectively comprise output data (also referred to herein as "sensor data") that corresponds to or may be correlated with a measure of odor being released from an associated garment. The soiled garment detection apparatus 104 comprises one or more sensors configured to transmit a measurable output signal to collectively form the output data produced by the soiled garment detection apparatus 104. The output data produced by the soiled garment detection apparatus 104 is transmitted over the network 106 to the controller 102 for processing for purposes of soiled garment detection. The controller 102 is also responsible for tracking and recording which instances of the soiled garment detection apparatus 104 correspond to particular garments of the collection of garments 108. In some embodiments, a particular garment is to be used with a particular instance of the soiled garment detection apparatus 104 throughout the lifetime of its use so as to maintain consistent readings. In other embodiments, the controller 102 may track the garments individually using an unique identifier of the garment, and in these embodiments, the garments need not be used with the same instance of the soiled garment detection apparatus 104.

As shown, the controller 102 comprises a receiver 114, an analysis module 116, a transmitter 118, a local data repository 120, and an interface module 122 all configured to communicate with each other (e.g., via a bus, shared memory, a switch, or application programming interfaces (APIs)). It will be appreciated that one or more these various components of the controller 102 may be combined into a single component. As an example, the transmitter 118 and receiver 114 may be combined (e.g., to share common circuitry or a single housing) to form a transceiver. Further, in some embodiments, one or more components may be omitted and additional components may also be included.

The receiver 114 is configured to interrogate each of the soiled garment detection apparatuses 104, and receive data therefrom. The data received from the soiled garment detection apparatus 104 includes the output data from the one or more sensors (e.g., the measure of odor) and, in some embodiments, an identifier of the corresponding garment 110-112.

The analysis module 116 is responsible for processing received output data to determine whether a particular garment is soiled and in need of laundering. To this end, the analysis module 116 analyzes the output data to determine whether the measure of odor released is above a threshold level of acceptable odor. If the odor released by the garment is at or below the threshold level of acceptable odor, the analysis module 116 determines that the garment is clean or, at least, not in need of laundering (e.g., not soiled). On the other hand, if the analysis module 116 determines that the odor released from the garment is above the threshold level for acceptable odor, the analysis module 116 determines that the garment is soiled.

Consistent with some embodiments, the measure of odor released by each of garments 110-112 is included in the output data produced by the soiled garment detection apparatus 104 and may include or be based on a concentration of certain particles (e.g., ammonia or amino acids) released by the garments 110-112 that commonly produce foul smelling odors, especially "body odor." Accordingly, the analysis module 116 may determine that the measure of odor released by the garments 110-112 is above the acceptable threshold level of odor based on the concentration of foul odor causing particles released by the garments 110-112 being above a particular threshold.

In some embodiments, the threshold level of acceptable odor may be configured by an administrator (e.g., a launderer of the collection of garments 108), or other user such that the odor level released by the garments 110-112 does not exceed a fairly standard level of acceptable odor (e.g., no foul odor) or such that the odor released by the garments 110-112 does not exceed an odor preference of the user.

In some instances, a garment may release an odor that is, although not foul or indicative of a soiled garment, detectable through human olfaction. For example, leather garments have a very distinct, although not foul, odor. Accordingly, in some embodiments, determining that a garment from the collection of garments 108 is soiled (e.g., that the odor released by the garment is above an acceptable threshold level of odor) may involve storing an initial set of output data from the soiled garment detection apparatus 104 to establish a baseline level of odor released by the each of the garments 110-112. The initial set of output data is received when each of the garments 110-112 is clean or recently laundered (as indicated by appropriate user input). In this manner, the analysis module 116 is enabled to recognize when the odor being released by each of the garments 110-112 has deviated from the "normal" odor released by the garments, and to what degree. In some embodiments, the threshold level of acceptable odor may be set according to an acceptable deviation from the baseline odor level.

Consistent with some embodiments, the controller 102 may establish and store (e.g., in the local repository 120) a dedicated olfactory profile for each of the garments in the collection of garments 108. The olfactory profile may include the baseline level of odor along with other information regarding a concentration of particles normally released by the garment. The olfactory profile may be based on information about the garment received from an intelligent garment tag associated with the garments 110-112 or received from the user via interface provided by the interface module 122. The olfactory profile specifies various concentrations of particles released by the garment by virtue of its fabric type or other intrinsic qualities. In this way, the analysis module 116 may be enabled to make informed determinations of whether the odor released by the garment is above an acceptable threshold level because the analysis module 116 is able to recognize that a certain amount of odor (e.g., a concentration of certain particles) is expected regardless of the state of the garment.

The analysis module 116 may track and record the output data corresponding to each garment of the collection of garments 108 throughout the lifetime of the garment. This information may be stored by the controller 102 in the local repository 120 along with the determined laundering status (e.g., clean or soiled). By tracking the sensor data over the lifetime of a garment, the analysis module 116 is able to track the degradation of the garment that occurs from wearing the garment. In some instances, the analysis module 116 may determine that a particular garment has exceeded a threshold level of degradation, and in response, the analysis module 116 works in conjunction with the interface module 112 to provide a user with a notification that the garment has degraded and should be replaced.

Further, in addition to determining whether a particular garment is simply clean or soiled, the analysis module 116 may analyze the output data to determine the degree to which a garment is either clean or soiled. The analysis module 116 may make this determination based on the tracked output data. For example, the analysis module 116 may determine the degree to which a garment is either clean or soiled based on how far above or below the measure of odor is from the predefined threshold or the baseline odor level. The degree to which the odor released by each of the garments 110-112 exceeds the threshold level for acceptable odor (e.g., the degree to which the garment is soiled) may be tracked and used in determining the urgency with which the garment is to be laundered. In other words, the analysis module 116 recognizes that the worse a garment smells, the more urgent the need to launder the garment. The degree to which the odor released by each of the garments 110-112 is below the threshold level for acceptable odor (e.g., the degree to which the garment is clean) may be tracked and used to provide the user with routine reminders to keep the user apprised of the cleanliness of his garments, which allows the user to anticipate future laundry cycles.

Upon determining that a garment from the collection of garments 108 is soiled, the analysis module 116 works in conjunction with the interface module 122 to transmit a message to a device (e.g., a smartphone) of a user associated with the collection of garments 108 (e.g., an owner of the garments) to notify the user of the soiled garment and to remind the user to launder the garment. Further, the analysis module 116 may work in conjunction with the transmitter 118 to provide control data to the soiled garment detection apparatus 104 that causes the soiled garment detection apparatus 104 to provide a soiled garment alert.

The transmitter 118 is responsible for providing (e.g., transmitting) control data to instances of the soiled garment detection apparatus 104. Accordingly, the transmitter 118 may comprise an antenna capable of wirelessly transmitting the control data to the soiled garment detection apparatus 104. The control data, once received by the soiled garment detection apparatus 104, causes an alert component of the soiled garment detection apparatus 104 to provide a soiled garment alert.

The local data repository 120 of the controller 102 is a machine-readable medium that stores information about the collection of garments 108. For example, the local data repository 1120 stores laundering information about each garment 110-112 in the collection of garments 108 along with an identifier of the corresponding soiled garment detection apparatus 104. In particular, the local data repository 120 stores a record of the laundering state (e.g., "clean" or "soiled") of each the garments 110-112 as determined by the analysis module 116. Accordingly, for garments that the analysis module 116 determines are releasing an odor below the acceptable threshold level of odor, the local data repository 120 stores a record associated with an identifier of the garment indicating that the garment is "clean." Conversely, for garments that the analysis module 116 determines are releasing an odor above the acceptable threshold level of odor, the local data repository 120 stores a record associated with an identifier of the garment indicating that the garment is "soiled." In some embodiments, the local data repository 120 may store a record of the output associated with the garment throughout the lifetime of the garment along with an indicator of the degree to which the garment is either clean or soiled.

The interface module 122 provides users of the soiled garment detection and notification system 100 with access to laundering information in the local data repository 120. Further, the interface module 122 is responsible for the generation and presentation of a number of graphical user interfaces (GUI) to present information to users. For example, the interface module 122 may generate and cause presentation of a GUI to present laundering information about the collection of garments 108 stored in the local data repository 120 of the controller 102. The interface module 122 may cause presentation of such a GUI by providing a user device with a set of instructions that cause the user device to present the GUI.

The interface module 122 is also responsible for the generation and delivery of messages to users of the soiled garment detection and notification system 100. Such messages may include a notification that a particular garment is soiled along with a suggested course of action to improve the odor being released by the garment (e.g., a suggestion to launder the garment). The interface module 122 may utilize any one of a number of message delivery networks and platforms to deliver messages to users. For example, the interface module 122 may deliver electronic mail (e-mail), instant message (IM), Short Message Service (SMS), text, facsimile, or voice (e.g., voice over IP (VoIP)) messages via the wired (e.g., the Internet), plain old telephone service (POTS), or wireless (e.g., mobile, cellular, WiFi, WiMAX) networks.

Figure 3:
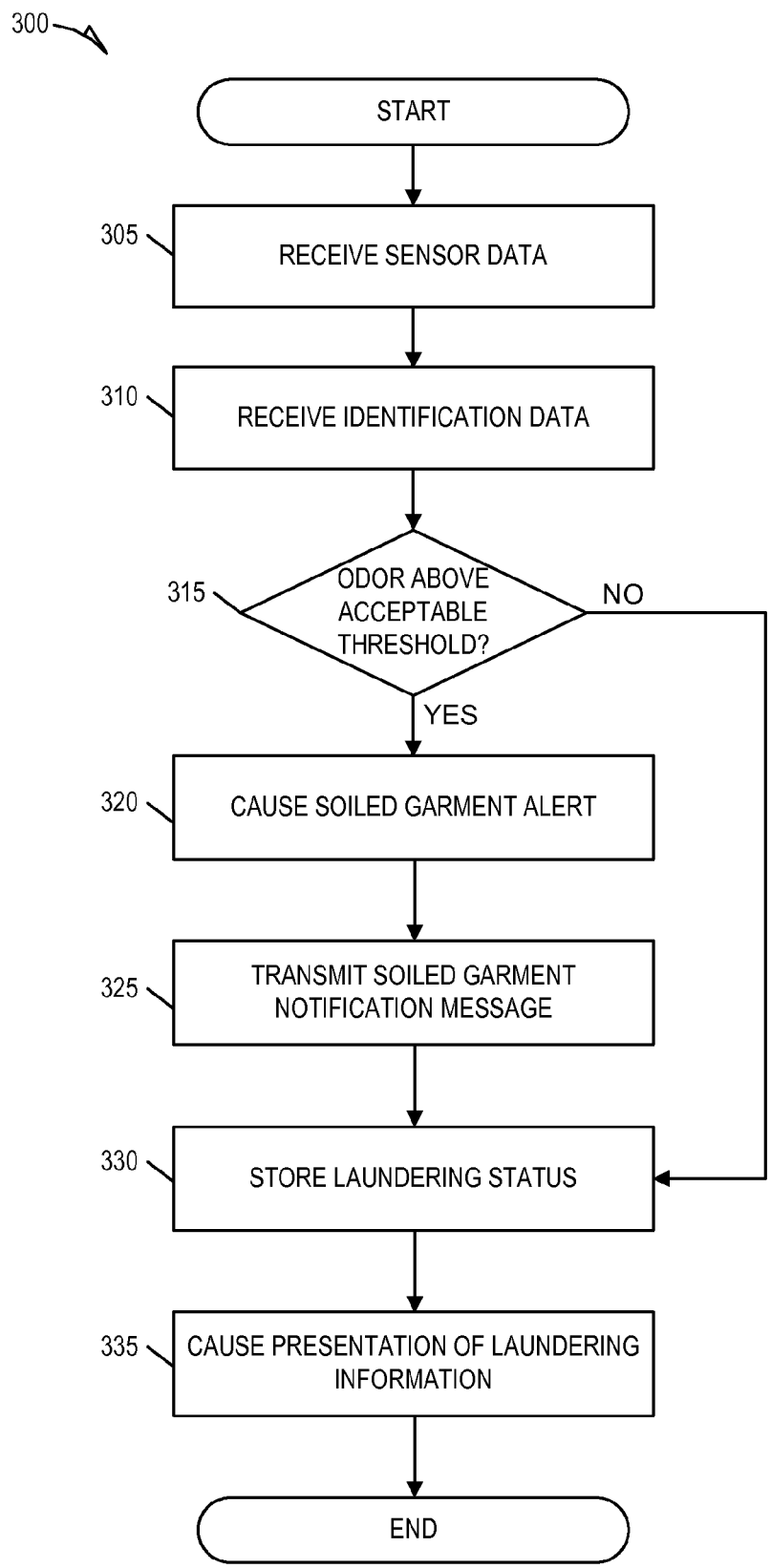
FIG. 3 is a flow chart illustrating a method for providing a soiled garment alert and notification, according to an example embodiment.

Although the controller 102 is illustrated to be in communication with three instances of the soiled garment detection apparatus 104, it shall be appreciated that the controller 102 may be in communication with fewer or additional instances of the soiled garment detection apparatus 104. In this manner, the controller 102 may serve as a central hub for controlling and exchanging data with a plurality of soiled garment detection apparatus 104. However, it shall be appreciated that in other embodiments, the controller 102 may be omitted, and multiple instances of the soiled garment detection apparatus 104 may communicate and exchange data without the need for the controller 102. Further, while the controller 102 is illustrated in FIG. 3 to form a stand-alone component, it shall be appreciated that, in other embodiments, the controller 102 may be implemented by a computer or be embedded in a laundering device (e.g., washing machine or clothes dryer) to provide additional functionality thereto. Moreover, in some embodiments, the controller 102 may be embedded in an instance of the soiled garment detection apparatus 104. Additionally, as is understood by skilled artisans in the relevant computer and Internet-related arts, each component (e.g., a module) illustrated in FIG. 1 may represent a hardware component, a set of hardware components, or a set of logic (e.g., executable software instructions) and the corresponding hardware (e.g., memory and processor) for executing the set of logic.

Figure 2:
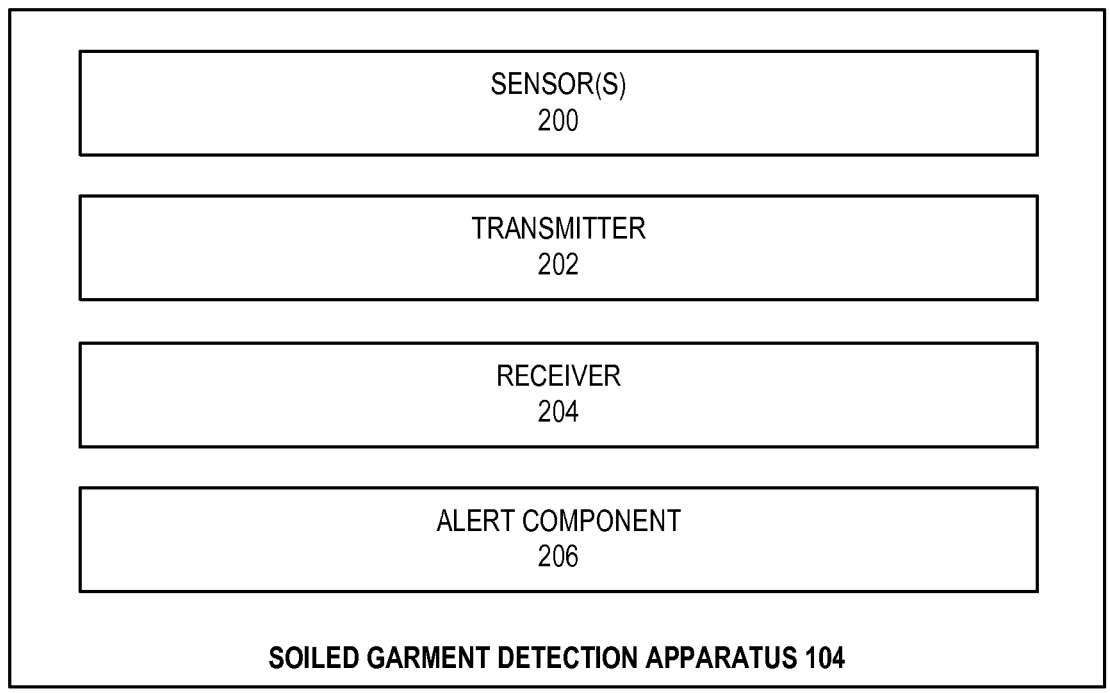
FIG. 2 is a block diagram illustrating various functional components of a soiled garment detection apparatus, which is provided as part of the soiled garment detection and notification system, according to an example embodiment.

FIG. 2 is a block diagram illustrating various functional components of a soiled garment detection apparatus 104, which is provided as part of the soiled garment detection and notification system 100, according to an example embodiment. As is understood by skilled artisans in the relevant computer and Internet-related arts, each component (e.g., a module) illustrated in FIG. 2 may represent a hardware component, a set of hardware components, or a set of logic (e.g., executable software instructions) and the corresponding hardware (e.g., memory and processor) for executing the set of logic. While the functional components of the soiled garment detection apparatus 104 are depicted and discussed in the singular sense, it will be appreciated that, in other embodiments, multiple instances of any one of these components may be employed.

The soiled garment detection apparatus 104 is illustrated in FIG. 2 as including one or more sensor(s) 200, a transmitter 202, a receiver 204, and an alert component 206, all configured to communicate with each other (e.g., via a bus, shared memory, a switch, or application programming interfaces (APIs)). It will be appreciated that one or more these various components of the soiled garment detection apparatus 104 may be combined into a single component. As an example, the transmitter 202 and receiver 204 may be combined (e.g., to share common circuitry or a single housing) to form a transceiver. Further, in some embodiments, one or more components may be omitted and additional components may also be included.

The one or more sensor(s) 200 are configured to respectively produce an output signal (e.g., an electrical signal) that corresponds to or may be correlated with a measure of odor released from garments. In particular, the sensor(s) 200 may include an olfactory sensor configured to measure a concentration (e.g., a number of particles per unit volume) of certain foul odor causing particles or compounds that may be released by a garment. Body odor (also known as "B.O.," "brohmhidrosis," "osmidrosis," and "ozochrotia"), for example, is a result of the breakdown of proteins into acids (e.g., propionic acid or isovaleric acid) by bacteria. Accordingly, by measuring the concentration of such particles (e.g., acids) on or near a garment, the olfactory sensors can provide the controller 102 with an indication of the odor being released by the garment, and thus, an indication of whether the garment is soiled. Collectively, the output signals from the one or more olfactory sensors 200 form olfactory sensor data (also referred to as "output data"). The olfactory sensor(s) 200 may employ a number of various sensors and detection techniques including, for example, conductive-polymer odor sensors, tin-oxide gas sensors, quartz-crystal micro-balance sensors, or physical litmus reactions.

In some embodiments, the sensor(s) 200 may include one or more moisture sensors configured to detect moisture levels of garments and chemical concentrations of the moisture causing agents. Similar to the olfactory sensors, the output provided by the moisture sensors (e.g., a moisture level) may provide the controller 102 with an indication of whether a garment is soiled. The moisture sensors may be employed in conjunction with or in the alternative to the olfactory sensors.

In some embodiments, the sensor(s) may include one or more visual sensors (e.g., ultra violet (UV) sensors or photo sensors) configured to measure and detect stains and other discoloring present on the garments. The visual sensors may be employed in conjunction with or in the alternative to the olfactory sensors or the moisture sensors. In these embodiments, the soiled garment detection and notification system 100 may further include one or more light emitting sources (e.g., ultra violet light source) positioned to emit light on the collection of garments 108, and the visual sensors (e.g., included as part of the sensor(s) 200) may be configured and positioned such that they are able detect the light reflected back from each of the garments 110-112. The resulting output (e.g., the measure of light reflected back from the garments 110-112) may be used by the controller 102 to determine whether stains or other discoloring is present on the garment. In some embodiments, the sensor(s) may include a camera configured to capture images of the garments 110-112 while the light emitting source is emitting light on the garments, and the images may be transmitted to the controller 102 for analysis to determine whether any one of the garments 110-112 are soiled. In some embodiments, the controller 102 may also use images produced by the camera to individually identify each garment of the collection of garments 108 by performing image recognition processing on the images.

The transmitter 202 is configured to transmit information to the controller 102. For example, the transmitter 202 provides olfactory sensor data produced by the one or more sensor(s) 200 to the controller 102. Additionally, the transmitter 202 may transmit an identifier of a garment along with other information about the garment to the controller 102.

The transmitter 202 may comprise an antenna capable of wirelessly transmitting the sensor data in one or many various frequencies and protocols over the network 106. For example, the transmitter 202 may comprise an antenna capable of transmitting the sensor data using a high-level personal area network protocol such as ZigBee. As another example, the transmitter 202 may comprise an antenna capable of transmitting a modulated radio-frequency (RF) signal. In yet another example, the transmitter 202 may comprise an antenna capable of transmitting the sensor data using a low energy data transmission protocol such as Bluetooth Low Energy (BLE).

The receiver 204 is configured to receive control data from the controller 102 that causes the alert component 206 to provide an alert. Accordingly, the receiver 204 may comprise an antenna capable of receiving data over the network 106 in a variety of protocols and frequencies. For example, the controller 102 may provide the receiver 204 with control data using a high-level personal area network protocol such as ZigBee. In another example, the control data received by the receiver 204 is provided as modulated RF signals. In yet another example, the data received by the receiver 204 is transmitted using a low energy data transmission protocol such as BLE.

In some embodiments, the receiver 204 may also be configured to obtain data from intelligent garment tags affixed or otherwise associated with garments. For example, an intelligent garment tag may be affixed to the garment 110 inside the collar at a location traditionally occupied by a printed clothing label. The intelligent garment tag stores information about the garment such as an identifier, a color, a fabric, and laundering information. Accordingly, the receiver 204 may be employed to obtain an identifier of the garment along information related to the garment's color and fabric, and laundering of the garment. The intelligent garment tag may be implemented using a radio frequency identification (RFID) device to exchange such information using radio-frequency (RF) signals. Accordingly, the receiver 204 may work in conjunction with the transmitter 202 to transmit a request or interrogatory signal (e.g., an encoded radio signal) to an intelligent garment tag, and in response, the receiver 204 is provided with an identifier of the garment and other additional information.

The alert component 206 is configured to provide soiled garment alerts. The alerts provided by the alert component 206 may be one of several types of human-detectable sensory alerts including visual or luminescent alerts (e.g., flashing lights), an auditory alert (e.g., a beep or other sound), or a haptic alert (e.g., a vibration). Accordingly, the alert component 206 may comprise one or more of the following to provide human-detectable sensory alerts: a light emitting component (e.g., a light emitting diode (LED) or light bulb), an electroacoustic transducer (e.g., a speaker), or a haptic actuator.

FIG. 3 is a flow chart illustrating a method 300 for providing a soiled garment alert and notification, according to an example embodiment. The method 300 may be embodied in computer-readable instructions for execution by a hardware component (e.g., a processor) such that the steps of the method 300 may be performed in part or in whole by the functional components of the controller 102, and accordingly, the method 300 is described below, by way of example with reference thereto. However, it shall be appreciated that the method 300 may be deployed on various other hardware configurations and is not intended to be limited to the controller 102.

At operation 305, the receiver 114 receives sensor data from the soiled garment detection apparatus 104. The sensor data may comprise olfactory sensor data that includes a measure of the concentration of foul odor causing particles released by a garment and, as such, provides a measure of odor being released by a garment. At operation 310, the receiver 204 receives identification data from the soiled garment detection apparatus 104. The identification data includes an identifier of the garment to distinguish the garment from other garments in a collection of garments (e.g., collection of garments 108) such as a group of garments stored in a closet. In some embodiments, the identifier may be first obtained (e.g., via RFID) by the soiled garment detection apparatus 104 from an intelligent garment tag affixed to the garment. In some embodiments, each garment in the collection of garments 108 may be initially assigned an identifier that is linked to the particular instance of the soiled garment detection apparatus 104 being used to monitor the garment. In some embodiments, the identifier of the garment may be obtained based on an analysis of image data received from a camera included as part of the soiled garment detection and notification system 100.

At operation 315, the analysis module 116 analyzes the sensor data to determine whether the measure of odor released by the garment exceeds an acceptable threshold level of odor. For example, the analysis module 116 may determine whether the concentration of foul odor causing particles, such as propionic and isovaleric acids, is above an acceptable threshold. The acceptable threshold level of odor may, for example, be based on user preferences, a comparison with a baseline odor measurement or information in the garment's olfactory profile, or various combinations thereof. In embodiments where the acceptable threshold level of odor is based on user preferences, the interface module 122 may provide a user interface for establishing user preferences with respect to the acceptable threshold level of odor.

In embodiments in which a moisture sensor is employed, the analysis module 116 may analyze the sensor data to determine whether the moisture level of the garment exceeds an acceptable threshold. Further, in embodiments in which a visual sensor is employed, the analysis module 116 may analyze the sensor data to determine whether the amount of discoloration of the garment exceeds an acceptable threshold.

In some embodiments, the analysis module 116 may determine whether the measure of odor released by the garment exceeds the acceptable threshold level of odor by comparing the current set of sensor data (e.g., the data received at operation 305) with a baseline odor level established from an initial set of sensor data received while the garment is freshly laundered (e.g., clean and unsoiled), and determining that the current set of olfactory sensor data deviates (e.g., is greater than) the baseline odor level by a predetermined percentage. Accordingly, the determination of whether the measure of odor exceeds the acceptable threshold may include receiving an indication from a user that a garment is freshly laundered (e.g., submitted via a user interface provided by the interface module 122), and storing an initial set of sensor data (e.g., received from the soiled garment detection apparatus 104) to establish the baseline odor level. The establishing of the baseline odor level may further include providing a user interface to input information about a particular garment (e.g., fabric size) that may impact the baseline odor level, and receiving the information entered through the user interface. The user interface may also be used to specify the predefined acceptable level of odor.

If the analysis module 116 determines that the measure of odor released by the garment exceeds the acceptable threshold level, the analysis module 116 causes the soiled garment detection apparatus 104 to provide a soiled garment alert at operation 320. Accordingly, the analysis module 116 may work in conjunction with the transmitter 118 to transmit a set of instructions to the soiled garment detection apparatus 104 that, when interpreted, cause the alert component 206 of the soiled garment detection apparatus 104 to provide a human-detectable alert.

At operation 325, the interface module 122 transmits a soiled garment notification message (e.g., a push notification) to a user device (e.g., a smartphone) of a user responsible for (e.g., an owner) the garment 110-112. The soiled garment notification message may include a notification that the garment is soiled, a suggested course of action, and the identifier of the garment to assist the user in identifying the garment. For example, the suggested course of action may be a reminder to launder the garment. As another example, the suggested course of action may be to switch laundry detergents to a brand that may be more suited to reduce foul odors from being released by the garment (e.g., a high concentration or extra strength detergent). In this example, the message may also include an item recommendation for a different brand of laundry detergent to accomplish such foul odor reduction.

Figures 4, 5:
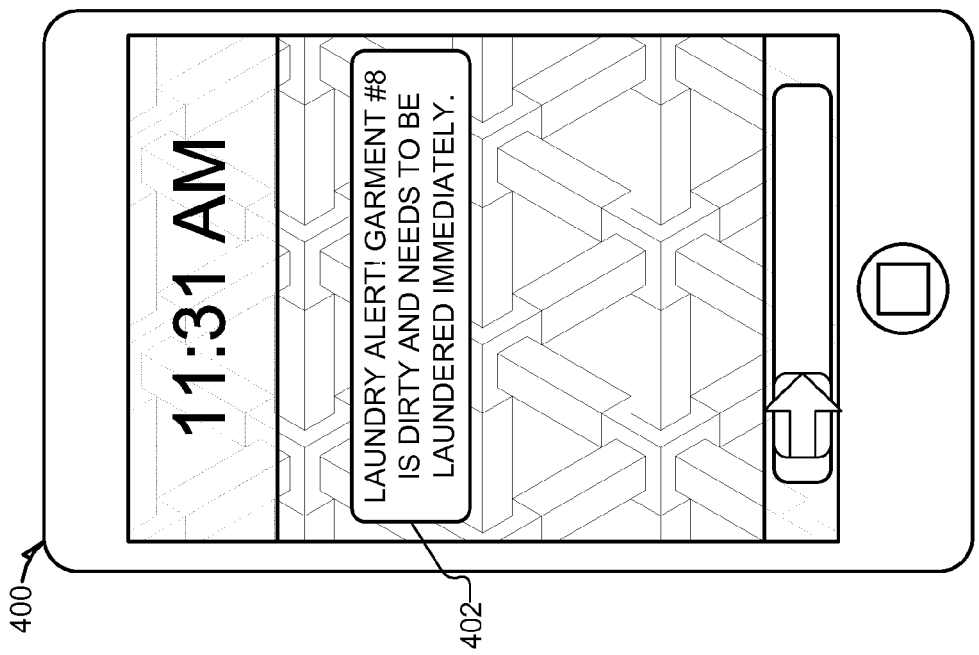
FIG. 4 is an interface diagram depicting a laundering alert received by and displayed on a user device, according to an example embodiment.
FIG. 5 is an interface diagram depicting a portion of an interface displaying laundering information for a collection of garments, according to an example embodiment.

As an example, FIG. 4 is an interface diagram depicting a soiled garment notification message 402 received by and displayed on a user device 400, according to an example embodiment. Although the user device 400 is illustrated in FIG. 4 to be a smart phone, it shall be appreciated that the user device 400 may be any of a variety of other types of devices (e.g., a tablet computer, a personal digital assistant (PDA), a personal navigation device (PND), a handheld computer, a desktop computer, a laptop or netbook, a wearable computing device, a Global Positioning System (GPS) device, a data enabled book reader, or a video game system console). As shown, the soiled garment notification message 402 includes a notification that the garment is soiled (the garment is indicated as being "dirty"), a reminder to launder the garment ("Garment . . . needs to be laundered"), and an identifier of the garment ("Garment #8).

Returning to FIG. 3, at operation 330, the controller 102 uses the identifier of the garment to store a record of a laundering status (e.g., "clean" or "soiled") of the garment in the local repository 120. The laundering status of the garment is based on the determination made at operation 315. In other words, if the analysis module 116 determines the odor released by the garment exceeds the acceptable threshold level of odor, the garment is assigned the laundering status of "soiled." Conversely, if the analysis module 116 determines the odor released by the garment is below the acceptable threshold level of odor, the garment is assigned the laundering status of "clean." Accordingly, if the analysis module 116 determines the odor released by the garment is below the acceptable threshold level of odor at operation 315, the controller 102 proceeds to directly store the laundering status of the garment 110-112 at operation 330.

At operation 335, the interface module 122 generates and causes presentation of an interface (e.g., on the user device 400) to display the laundering status information of a collection of garments (e.g., stored in the local repository 120). The interface may, for example, include identifiers of a plurality of garments, a corresponding laundering status, and additional laundering information.

As an example, FIG. 5 is an interface diagram depicting a portion of an interface 500 displaying laundering information for a collection of garments, according to an example embodiment. As shown, the interface 500 includes table 502, which presents laundering information for a collection of garments (e.g., the collection of garments 108). Identifiers of each garment are provided in column 504. Column 506 includes a laundering status (e.g., "clean" or "soiled") for each garment identified in column 504. Column 508 includes additional laundering information related to the urgency with which soiled garments are to be laundered. The urgency with which soiled garments are to be laundered may, for example, depend on the degree to which the odor being released by the garment exceeds the acceptable level of odor. Accordingly, in addition to determining whether the odor being released by a garment exceeds a threshold level for acceptable odor, the analysis module 116 also determines the degree to which the odor exceeds or is below the threshold.

Figure 6:
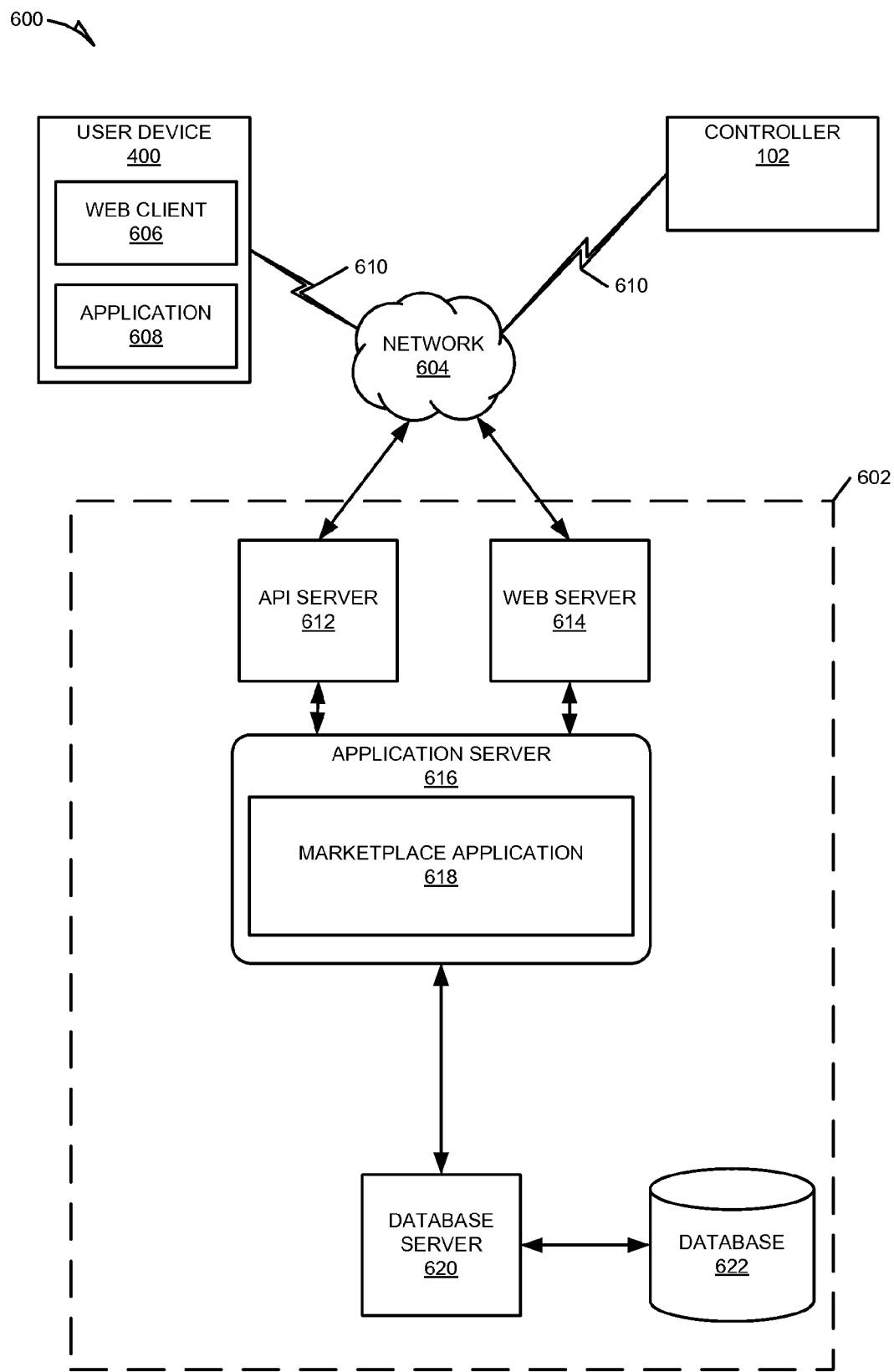
FIG. 6 is a network diagram depicting a network system having a client-server architecture configured for exchanging data between a user device, a controller, and a network-based marketplace, consistent with some embodiments.

FIG. 6 is a network diagram depicting a network system 600 having a client-server architecture configured for exchanging data between the user device 400, the controller 102, and a network-based marketplace 602, consistent with some embodiments. The network-based marketplace 602 communicates and exchanges data within the network system 600 that pertains to various functions and aspects associated with the network system 600 and its users. The network-based marketplace 602 may provide server-side functionality, via a network 604 (e.g., the Internet), to the user device 400 and the controller 102. The user device 400 and controller 102 may exchange data with the network-based marketplace 602. These data exchanges may include transmitting, receiving, and processing data to, from, and regarding content and users of the network system 600. The data may include, but are not limited to: laundering information; sensor data; images; video or audio content; user preferences; product and service feedback, advice, and reviews; product, service, manufacturer, and vendor recommendations and identifiers; product and service listings associated with buyers and sellers; product and service advertisements; auction bids; transaction data; and social data, among other things.

In various embodiments, the data exchanged within the network system 600 may be dependent upon user-selected functions available through one or more client or user interfaces (UIs). The UIs may, for example, be specifically associated with a web client 606 (e.g., a browser) executing on the user device 400, and in communication with the network-based marketplace 602. The UIs may also be associated with application 608 executing on the user device 400, such as a client application designed for interacting with the controller 102 or the network-based marketplace 602. The application 608 may, for example, provide users with the ability to communicate with the controller 102, monitor the laundering status of a collection of garments, receive soiled garment and laundering notifications, and receive product recommendations related to soiled garments.

The user device 400 and the controller 102 may interface with the network 604 (e.g., the Internet or wide area network (WAN)) via a connection 610, which may be any of a variety of types of connections. For example, the connection 610 may be a wireless fidelity (Wi-Fi, IEEE 802.33x type) connection, a Worldwide Interoperability for Microwave Access (WiMAX) connection, or another type of wireless data connection. In such an embodiment, the network 604 may include one or more wireless access points coupled to a local area network (LAN), a WAN, the Internet, or other packet-switched data network. In another example, the connection 610 may be a wired connection, for example an Ethernet link, and the communication network 604 may be a LAN, a WAN, the Internet, or other packet-switched data network. Accordingly, a variety of different configurations are expressly contemplated.

In some embodiments, depending on the form and location of the user device 400, the connection 610 employed by the user device 400 may be different than the connection 610 employed by the controller 102. For example, the connection 610 of the user device 400 may be Code Division Multiple Access (CDMA) connection, a Global System for Mobile communications (GSM) connection, or other type of cellular connection. Such a connection 610 may implement any of a variety of types of data transfer technology, such as Single Carrier Radio Transmission Technology (3×RTT), Evolution-Data Optimized (EVDO) technology, General Packet Radio Service (GPRS) technology, Enhanced Data rates for GSM Evolution (EDGE) technology, or other data transfer technology (e.g., fourth generation wireless, 4G networks). When such technology is employed, the network 604 may include a cellular network that has a plurality of cell sites of overlapping geographic coverage, interconnected by cellular telephone exchanges. These cellular telephone exchanges may be coupled to a network backbone (e.g., the public switched telephone network (PSTN), a packet-switched data network, or to other types of networks).

Turning specifically to the network-based marketplace 602, an API server 612 and a web server 614 are coupled to (e.g., via wired or wireless interfaces), and provide programmatic and web interfaces respectively to, an application server 616. The application server 616 may, for example, host one or more applications, such as a marketplace application 618. The marketplace application 618 provides a number of marketplace functions and services to users that access the network-based marketplace 602. For example, the marketplace application 618 may provide a number of publishing, listing, and price-setting mechanisms whereby a seller may list (or publish information concerning) goods or services for sale, a buyer can express interest in or indicate a desire to purchase such goods or services, and a price can be set for a transaction pertaining to the goods or services.

As illustrated in FIG. 6, the application server 616 is coupled to a database server 620 that facilitates access to the database 622. In some embodiments, the database 622 may include multiple databases that may be internal or external to the network-based marketplace 602. The database 622 stores data pertaining to various functions and aspects associated with the network system 600 and its users. For example, user accounts for users of the network-based marketplace 602 may be stored and maintained in the database 622.

Each user account may comprise user data that describes aspects of a particular user. The user data may include demographic data, social data, user preferences, and financial information. The demographic data may, for example, include information describing one or more characteristics of a user. Demographic data may, for example, include gender, age, location information, employment history, education history, contact information, familial relations, or user interests. The financial information may, for example, include private financial information of the user such as account number, credential, password, device identifier, user name, phone number, credit card information, bank information, transaction history or other financial information which may be used to facilitate online transactions by the user. The transaction history includes information related to transactions for goods or services (collectively referred to as "items" or "products") that may be offered for sale by merchants using marketplace services provided by the network-based marketplace 602. The transaction history information may, for example, include a description of a product purchased by the user, an identifier of the product, a category to which the product belongs, a purchase price, a quantity, or a number of bids.

It shall be appreciated that although the various functional components of the network system 600 are discussed in the singular sense, multiple instances of one of more of the various functional components may be employed. Moreover, while the network system 600 shown in FIG. 6 employs a client-server architecture, the present inventive subject matter is, of course, not limited to such an architecture, and could equally well find application in an event-driven, distributed, or peer-to-peer architecture system, for example.

Figure 7:
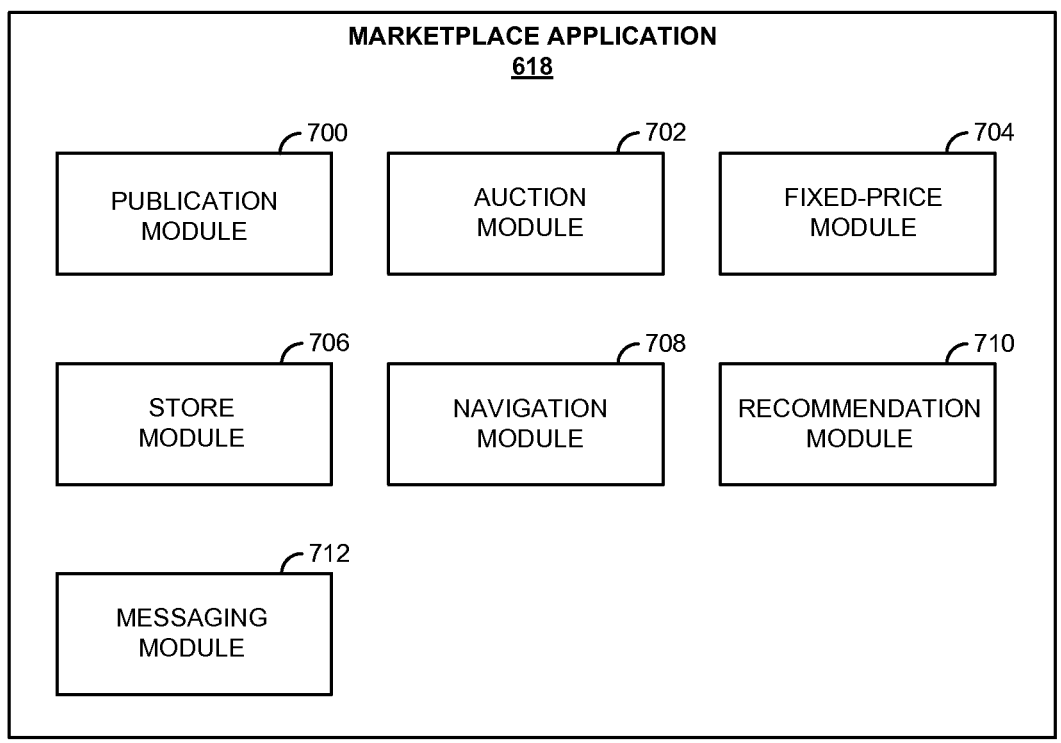
FIG. 7 is a block diagram illustrating multiple modules forming the marketplace application, according to an example embodiment.

FIG. 7 is a block diagram illustrating an example embodiment of multiple modules forming the marketplace application 618. As is understood by skilled artisans in the relevant computer and Internet-related arts, each component (e.g., a module or engine) illustrated in FIG. 7 may represent a set of logic (e.g., executable software instructions) and the corresponding hardware (e.g., memory and processor) for executing the set of logic. Further, each of the components (e.g., a module or engine) illustrated in FIG. 7 is communicatively coupled (e.g., via appropriate interfaces) to the other components and to various data sources, so as to allow information to be passed between the components or so as to allow the components to share and access common data. Moreover, each component illustrated in FIG. 7 may be hosted on dedicated or shared server machines that are communicatively coupled to enable communications between server machines. The various components illustrated in FIG. 7 may furthermore access the databases 622.

The marketplace application 618 may provide a number of publishing, listing, and price-setting mechanisms whereby a seller may list (or publish information concerning) goods or services for sale, a buyer can express interest in or indicate a desire to purchase such goods or services, and a price can be set for a transaction pertaining to the goods or services. To this end, the marketplace application 618 is shown to include a publication module 700 and an auction module 702, which support auction-format listing and price setting mechanisms (e.g., English, Dutch, Vickrey, Chinese, Double, Reverse auctions etc.). The auction module 702 may also provide a number of features in support of such auction-format listings, such as a reserve price feature whereby a seller may specify a reserve price in connection with a listing, and a proxy-bidding feature whereby a bidder may invoke automated proxy bidding.

A fixed-price module 704 may support fixed-price listing formats (e.g., the traditional classified advertisement-type listing or a catalogue listing) and buyout-type listings. Specifically, buyout-type listings (e.g., including the Buy-It-Now (BIN) technology developed by eBay Inc., of San Jose, Calif.) may be offered in conjunction with auction-format listings, and allow a buyer to purchase goods or services, which are also being offered for sale via an auction, for a fixed-price that is typically higher than the starting price of the auction.

A store module 706 may allow sellers to group their product listings (e.g., goods and/or services) within a "virtual" store, which may be branded and otherwise personalized by and for the sellers. Such a virtual store may also offer promotions, incentives, and features that are specific and personalized to a relevant seller. In one embodiment, the listings or transactions associated with the virtual store and its features may be provided to one or more users.

Navigation of the network-based marketplace 602 may be facilitated by a navigation module 708. For example, the navigation module 708 may, inter alia, enable keyword searches of listings published via the network-based marketplace 602. The navigation module 708 may also allow users, via a sales-associated UI, to browse various category, catalog, inventory, social network, and review data structures within the network-based marketplace 602. Various other navigation modules 708 (e.g., an external search engine) may be provided to supplement the search and browsing modules.

A recommendation module 710 provides item recommendation services and functions to users. The recommendation module 710 may receive requests for recommendations, and, in turn, provide a recommendation to the user based, at least in part, on information about the user maintained as part of a user account (e.g., previous products purchased by the user, a web page viewed by the user, an item given favorable feedback by the user, or items owned by the user). The recommendation module 710 may also automatically generate and provide item recommendations based on sensor data provided by the controller 102. For example, recommendations may be based on a concentration of certain odor causing particles indicated by the sensor data. Such recommendations may include one or more items (e.g., products or services) offered for sale that may replace the user's garments, assist the user in laundering soiled garments, improve an odor produced by the user, or improve an odor released by the garment.

As an example, upon receiving sensor data (e.g., from the controller 102) indicating that a particular garment is releasing a large concentration of odor causing particles, the recommendation module 710 may identify a garment made of natural fibers (e.g., wool, silk, or cotton) that may allow the skin of the garment wearer to better "breathe," which may result in better evaporation of sweat, and thus, fewer odor causing particles being released. The recommendation module 710 may then generate an item recommendation for the garment wearer that includes the garment. As another example, the recommendation module 710 may identify and recommend a new garment to replace a garment that the analysis module 116 has determined is too degraded for the user to continue to wear. As yet another example, the recommendation module 710 may suggest that a user sell a garment that is infrequently worn (as determined by the sensor data corresponding to the garment throughout the lifetime of the garment).

A messaging module 712 is responsible for generation and delivery of messages to users of the network system

600. Such messages may, for example, include item recommendations generated by the recommendation module 710. The messaging module 712 may utilize any one of a number of message delivery networks and platforms to deliver messages to users (e.g., e-mail, IM, SMS, text, facsimile, or voice messages). In some embodiments, the messaging module 712 may work in conjunction with the interface module 122 of the controller 102 to deliver messages to users.

Figure 8:
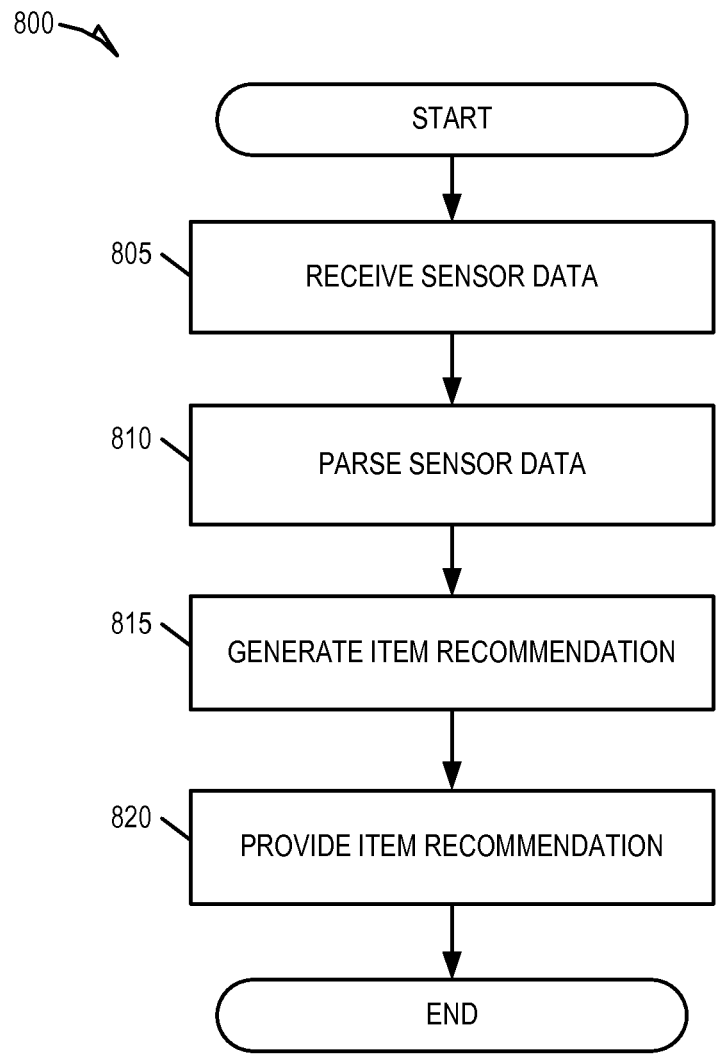
FIG. 8 is a flowchart illustrating a method for providing an item recommendation based on sensor data, according to an example embodiment.

FIG. 8 is a flowchart illustrating a method 800 for providing an item recommendation based on sensor data, according to an example embodiment. The method 800 may be embodied in computer-readable instructions for execution by a hardware component (e.g., a processor) such that the steps of the method 800 may be performed in part or in whole by the components of the application server 616, and accordingly, the method 800 is described below, by way of example with reference thereto. However, it shall be appreciated that the method 800 may be deployed on various other hardware configurations and is not intended to be limited to the application server 616. For example, the method 800 may be deployed for execution on the controller 102.

At operation 805, the application server 616 receives sensor data produced by a soiled garment detection apparatus 104 from the controller 102. In some embodiments, the sensor data is received directly from the controller 102. The sensor data received by the application server 616 may, for example, include a measure of a concentration of particles released by the garment. At operation 810, the recommendation module 710 parses the sensor data. For example, the recommendation module 710 may parse the sensor data to determine concentrations of certain odor causing particles (e.g., propionic and isovaleric acid) that are being released by the garment.

At operation 815, the recommendation module 710 generates an item recommendation based on the sensor data (e.g., the concentration of the odor causing particles). The recommendation generated by the recommendation module 710 may, for example, be based on concentrations of certain particles exceeding certain threshold levels or based on a garment exceeding a predefined level of degradation. In some instances, the recommendation module 710 may generate the item recommendation by identifying an item to assist with or employ in the process of laundering the garment (e.g., laundry detergent). In some instances, the recommendation module 710 may generate the item recommendation by identifying an item offered for sale that may reduce or help to reduce the concentration of odor causing particles that are released by the garment. The identifying of items for use as an item recommendation may include accessing a lookup table that includes a list of products known to improve concentrations of certain particles produced by the human body.

As an example of the foregoing operation, upon receiving sensor data (e.g., from the controller 102) indicating that a particular garment is releasing a large concentration of body odor causing particles, the recommendation module 710 may identify a particular deodorant that will help reduce the amount of body odor causing particles produced by a wearer of the garment (e.g., by making the environment more difficult for bacteria, which ultimately cause the release of odor causing particles, to thrive). The recommendation module 710 may then generate an item recommendation for the garment wearer that includes the deodorant.

At operation 820, the messaging module 712 transmits an item recommendation message to the user device 400. The item recommendation message may identify the item and include a link (e.g., a uniform resource locator (URL)) to a product listing (e.g., published using the marketplace application 618) from which the item may be purchased. The message may further include a rationale for providing the particular item in a recommendation (e.g., the item may improve the odor released by the garments of the user).

Modules, Components, and Logic

Certain embodiments are described herein as including logic or a number of components, modules, or mechanisms. Modules may constitute either software modules (e.g., code embodied on a machine-readable medium) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a Field-Programmable Gate Array (FPGA) or an Application Specific Integrated Circuit (ASIC). A hardware module may also include programmable logic or circuitry that is temporarily configured by software to perform certain operations. For example, a hardware module may include software executed by a general-purpose processor or other programmable processor. Once configured by such software, hardware modules become specific machines (or specific components of a machine) uniquely tailored to perform the configured functions and are no longer general-purpose processors. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times. Software accordingly configures a particular processor or processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, with a particular processor or processors being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented modules may be located in a single geographic location (e.g., within a home environment, an office environment, or a server farm). In other example embodiments, the processors or processor-implemented modules may be distributed across a number of geographic locations.

Example Machine Architecture and Machine-Readable

Figure 9:
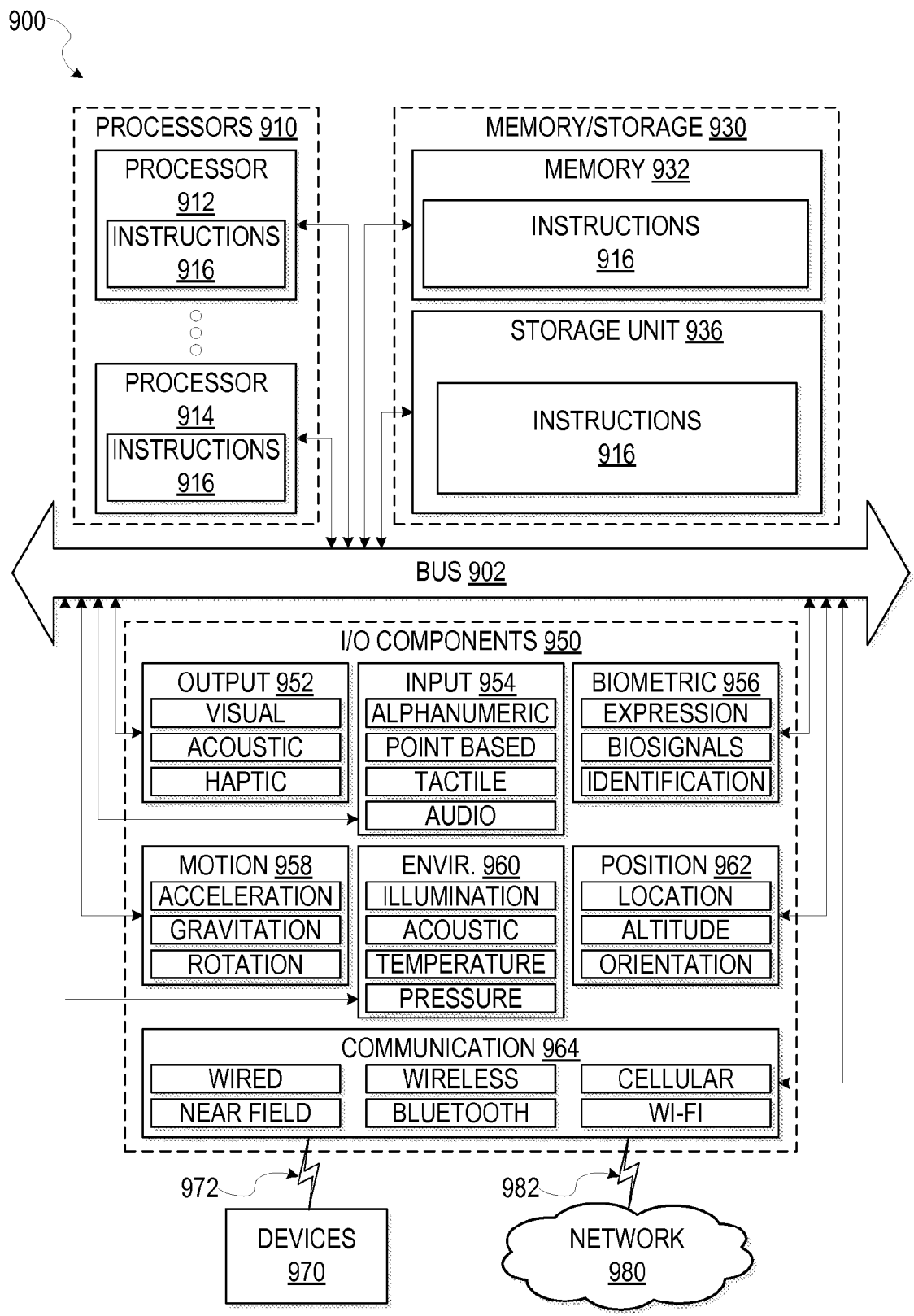
FIG. 9 is a diagrammatic representation of a machine in the example form of a computer system within which a set of instructions for causing the machine to perform any one or more of the methodologies discussed herein may be executed.

FIG. 9 is a block diagram illustrating components of a machine 900, according to some example embodiments, able to read instructions from a machine-readable medium (e.g., a machine-readable storage medium) and perform any one or more of the methodologies discussed herein. Specifically, FIG. 9 shows a diagrammatic representation of the machine 900 in the example form of a computer system, within which instructions 916 (e.g., software, a program, an application, an applet, an app, or other executable code) for causing the machine 900 to perform any one or more of the methodologies discussed herein may be executed. For example the instructions may cause the machine to execute the flow diagrams of FIGS. 3 and 8. Additionally, or alternatively, the machine 900 may correspond to the controller 102, and the instructions 916 may implement one or more components forming the controller 102. Further, in some embodiments, the machine 900 may correspond to the user device 400. The instructions transform the general, non-programmed machine into a particular machine programmed to carry out the described and illustrated functions in the manner described. In alternative embodiments, the machine 900 operates as a standalone device or may be coupled (e.g., networked) to other machines. In a networked deployment, the machine 900 may operate in the capacity of a server machine or a client machine in a server-client network environment, or as a peer machine in a peer-to-peer (or distributed) network environment. The machine 900 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 916, sequentially or otherwise, that specify actions to be taken by machine 900. Further, while only a single machine 900 is illustrated, the term "machine" shall also be taken to include a collection of machines 900 that individually or jointly execute the instructions 916 to perform any one or more of the methodologies discussed herein.

The machine 900 may include processors 910, memory 930, and I/O components 950, which may be configured to communicate with each other such as via a bus 902. In an example embodiment, the processors 910 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 912 and processor 914 that may execute instructions 916. The term "processor" is intended to include multi-core processor that may comprise two or more independent processors (sometimes referred to as "cores") that may execute instructions contemporaneously. Although FIG. 9 shows multiple processors, the machine 900 may include a single processor with a single core, a single processor with multiple cores (e.g., a multi-core process), multiple processors with a single core, multiple processors with multiples cores, or any combination thereof The memory/storage 930 may include a memory 932, such as a main memory, or other memory storage, and a storage unit 936, both accessible to the processors 910 such as via the bus 902. The storage unit 936 and memory 932 store the instructions 916 embodying any one or more of the methodologies or functions described herein. The instructions 916 may also reside, completely or partially, within the memory 932, within the storage unit 936, within at least one of the processors 910 (e.g., within the processor's cache memory), or any suitable combination thereof, during execution thereof by the machine 900. Accordingly, the memory 932, the storage unit 936, and the memory of processors 910 are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 916. The term "machine-readable medium" shall also be taken to include any medium, or combination of multiple media, that is capable of storing instructions (e.g., instructions 916) for execution by a machine (e.g., machine 900), such that the instructions, when executed by one or more processors of the machine 900 (e.g., processors 910), cause the machine 900 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 950 may include a wide variety of components to receive input, provide output, produce output, transmit information, exchange information, capture measurements, and so on. The specific I/O components 950 that are included in a particular machine will depend on the type of machine. For example, portable machines such as mobile phones will likely include a touch input device or other such input mechanisms, while a headless server machine will likely not include such a touch input device. It will be appreciated that the I/O components 950 may include many other components that are not shown in FIG. 9. The I/O components 950 are grouped according to functionality merely for simplifying the following discussion and the grouping is in no way limiting. In various example embodiments, the I/O components 950 may include output components 952 and input components 954. The output components 952 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 954 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 950 may include biometric components 956, motion components 958, environmental components 960, or position components 962 among a wide array of other components. For example, the biometric components 956 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 958 may include acceleration sensor components (e.g., accelerometer), gravitation sensor components, rotation sensor components (e.g., gyroscope), and so forth. The environmental components 960 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 962 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 950 may include communication components 964 operable to couple the machine 900 to a network 980 or devices 970 via coupling 982 and coupling 972 respectively. For example, the communication components 964 may include a network interface component or other suitable device to interface with the network 980. In further examples, communication components 964 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 970 may be another machine or any of a wide variety of peripheral devices (e.g., a peripheral device coupled via a Universal Serial Bus (USB)).

Moreover, the communication components 964 may detect identifiers or include components operable to detect identifiers. For example, the communication components 964 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 964, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 980 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 980 or a portion of the network 980 may include a wireless or cellular network and the coupling 982 may be a Code Division Multiple Access (CDMA) connection, a Global System for Mobile communications (GSM) connection, or other type of cellular or wireless coupling. In this example, the coupling 982 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 916 may be transmitted or received over the network 980 using a transmission medium via a network interface device (e.g., a network interface component included in the communication components 964) and utilizing any one of a number of well-known transfer protocols (e.g., hypertext transfer protocol (HTTP)). Similarly, the instructions 916 may be transmitted or received using a transmission medium via the coupling 972 (e.g., a peer-to-peer coupling) to devices 970. The term "transmission medium" shall be taken to include any intangible medium that is capable of storing, encoding, or carrying instructions 916 for execution by the machine 900, and includes digital or analog communications signals or other intangible medium to facilitate communication of such software.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

In this document, the terms "a" or "an" are used, as is common in patent documents, to include one or more than one, independent of any other instances or usages of "at least one" or "one or more." In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim. Moreover, in the following claims, the terms "first," "second," "third," and so forth are used merely as labels, and are not intended to impose numerical requirements on their objects.

What is claimed is:

1. A system for soiled garment detection and notification, the system comprising:
   a controller comprising:
      a receiver configured to receive, from a soiled garment detection apparatus, sensor data comprising a measure of odor being released by a garment;
      an analysis module, comprising one or more processors, configured to determine that the measure of odor exceeds an acceptable threshold level of odor by comparing the sensor data with a baseline odor level of the garment; and
      an interface module configured to transmit a message to a user device in response to the analysis module determining that the measure of odor exceeds the acceptable threshold of odor, the message including a notification related to the measure of odor being released by the garment.

2. The system of claim 1, further comprising a soiled garment detection apparatus, the soiled garment detection apparatus including:
   an olfactory sensor configured to produce sensor data comprising the measure of odor released from the garment;
   a transmitter coupled to the olfactory sensor, the transmitter configured to transmit the olfactory sensor data to the controller; and
   an alert component configured to produce a human-detectable alert.

3. The system of claim 2, wherein the controller further comprises a transmitter configured to transmit control data to the soiled garment detection apparatus, the control data to cause the alert component to produce the human-detectable alert in response to determining the measure of odor exceeds the acceptable threshold level of odor.

4. The system of claim 2, wherein the soiled garment detection apparatus further includes a radio frequency identification (RFID) reader configured to obtain an identifier of the garment from an RFID tag affixed to the garment, the transmitter being further configured to transmit the identifier of the garment to the controller.

5. The system of claim 4, wherein the message includes the identifier of the garment.

6. The system of claim 1, wherein the controller further comprises a local data repository to store laundering information related to a collection of garments, the garment being included in the collection of garments, the local data repository including a laundering status for the garment, the laundering status being based on the measure of odor being released by the garment.

7. The system of claim 6, wherein the interface module is further configured to generate a user interface to display at least a portion of the laundering information stored in the local data repository.

8. The system of claim 1, wherein the analysis module is configured to determine the measure of odor exceeds the acceptable threshold level of odor by performing further operations including:
   establishing an olfactory profile for the garment, the olfactory profile including the baseline odor level of the garment and information regarding a concentration of particles normally released by the garment; and
   comparing the sensor data to information in the olfactory profile.

9. A method comprising:
   receiving, from a soiled garment detection apparatus, sensor data comprising a measure of odor being released by a garment;
   determining, by a hardware processor, that the measure of odor exceeds an acceptable threshold level of odor based on a comparison of the sensor data with a baseline odor level of the garment; and
   in response to determining the measure of odor exceeds the acceptable threshold level of odor, transmitting a message to a user device, the message including a notification related to the measure of odor being released by the garment.

10. The method of claim 9, further comprising transmitting control data to a soiled garment detection apparatus in response to determining the measure of odor exceeds the acceptable threshold level of odor, the control data causing the soiled garment detection apparatus to provide a human-detectable alert.

11. The method of claim 9, further comprising generating an item recommendation based on the measure of odor released by the garment, the item recommendation including an item likely to improve the measure of odor normally released by the garment, the item recommendation being included in the message transmitted to the user device.

12. The method of claim 9, further comprising:
   storing a record of a laundering status of the garment in a local data repository, the local data repository including laundering information related to a plurality of garments, the laundering status being based on the measure of odor being released by the garment; and
   causing presentation of user interface including a portion of information stored in the local data repository.

13. The method of claim 9, further comprising receiving, from the soiled garment detection apparatus, an identifier of the garment, the identifier of the garment being included in the message.

14. The method of claim 9, further comprising establishing an olfactory profile specific to the garment, the olfactory profile including the baseline odor level of the garment and information regarding a concentration of particles released by the garment.

15. The method of claim 14, wherein the determining the measure of odor exceeds the acceptable threshold level of odor is further based on a comparison of the sensor data with information in the olfactory profile.

16. The method of claim 9, wherein the determining that the measure of odor exceeds the acceptable threshold level of odor comprises:
   storing initial sensor data to establish the baseline odor level for the garment, the initial sensor data being received from the soiled garment detection apparatus when the garment is freshly laundered;
   comparing the sensor data with the baseline odor level; and
   determining that the sensor data exceeds the baseline odor level by at least a predetermined percentage.

17. The method of claim 9, wherein the message further includes a suggested course of action to improve the measure of odor being released by the garment.

18. The method of claim 17, wherein the suggested course of action is a reminder to launder the garment.

19. A tangible machine-readable storage device embodying instructions that, when executed by at least on processor of a machine, cause the machine to perform operations comprising:
   receiving sensor data comprising a measure of odor being released by a garment;
   determining that the measure of odor exceeds an acceptable threshold level of odor based on a comparison of the sensor data with a baseline odor level of the garment; and
   in response to determining that the measure of odor exceeds the acceptable threshold level of odor, transmitting a message to a user device, the message including a notification related to the measure of odor being released by the garment.

* * * * *